(12) United States Patent
Wang et al.

(10) Patent No.: US 10,517,552 B2
(45) Date of Patent: Dec. 31, 2019

(54) DETECTOR SUPPORTING APPARATUS AND AN X-RAY IMAGING DEVICE

(71) Applicant: GENERAL ELECTRIC COMPANY, Schenectady, NY (US)

(72) Inventors: Yunfa Wang, Beijing (CN); Fusheng Li, Beijing (CN); Yuqing Li, Beijing (CN); Peng Qi, Beijing (CN); Huimin He, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 135 days.

(21) Appl. No.: 15/828,047

(22) Filed: Nov. 30, 2017

(65) Prior Publication Data

US 2018/0146939 A1    May 31, 2018

(30) Foreign Application Priority Data

Nov. 30, 2016   (CN) .......................... 2016 1 1082327

(51) Int. Cl.
*G03B 42/02*  (2006.01)
*A61B 6/00*  (2006.01)
*H05G 1/02*  (2006.01)

(52) U.S. Cl.
CPC .............. *A61B 6/4429* (2013.01); *A61B 6/54* (2013.01); *G03B 42/02* (2013.01); *H05G 1/02* (2013.01)

(58) Field of Classification Search
CPC .......... A61B 6/4429; A61B 6/54; H05G 1/02; G03B 42/02
See application file for complete search history.

(56) References Cited

U.S. PATENT DOCUMENTS

| 7,144,157 | B2* | 12/2006 | Dippl | G03B 42/02 378/177 |
| 7,775,712 | B1* | 8/2010 | Thieman | G03B 42/04 378/186 |
| 2016/0029984 | A1* | 2/2016 | Jang | A61B 6/4429 378/189 |
| 2018/0146939 | A1* | 5/2018 | Wang | A61B 6/4429 |

* cited by examiner

*Primary Examiner* — Kiho Kim
(74) *Attorney, Agent, or Firm* — Fletcher Yoder, P.C.

(57) ABSTRACT

A detector support device is described comprising a bracket, slide and detector trays, a connector and a cable. The connector comprises detector and cable interfaces, wherein the detector interface is installed on the detector tray to connect to the detector, and an accommodation cavity, in which the cable interface is located, is opened from an upper surface of the slide tray. A first fixing portion fixed to a bottom wall of the accommodation cavity and a first bending portion extending from the first fixing portion to a first end of the cable are also provided between the first end and a second end of the cable, the first end of the cable extends out of the slide tray so as to be connected to an external connector, and the second end of the cable is connected to the cable interface.

18 Claims, 4 Drawing Sheets

DETECTOR SUPPORTING APPARATUS AND AN X-RAY IMAGING DEVICE

TECHNICAL FIELD

The present disclosure relates to the field of medical imaging, and in particular to a detector support device and an X-ray imaging apparatus.

BACKGROUND

In an X-ray imaging apparatus such as an X-ray machine, an X-ray bulb tube may be provided on an upright column or a suspension arm, and is opposite a bed surface of a detection bed, wherein the bed surface of the detection bed is used for supporting a human body to be detected; when performing an X-ray imaging for the human body, the X-ray bulb tube emits X-rays which penetrate the human body; a detector for receiving the X-rays which penetrate the human body is provided at the back of the detection bed; and the X-rays received by the detector are converted into image signals, so that an image of a physiological structure of the human body can be obtained.

In one installation manner of the above-mentioned detector, the detector is placed on a tray, wherein the tray is installed at the back of the detection bed and is capable of being pulled out from one side of the detection bed, such that it is convenient for an operator to remove the detector from the tray so as to charge the detector.

In order to image different portions of the human body, the detector may also rotate to different positions in the tray so as to receive the X-rays.

In the prior art, a system connection between a detector and an image is re-established mostly in a wireless manner, for example, by providing a detector interface in the rear of the detector, such that after the detector is installed in the tray, an interface of the detector is directly connected to an interface located on the other side of the detection bed, so as to transmit signals to an image reconstruction system via the interface on the other side of the detection bed.

However, with constant upgrade of products, the imaging requirements for an X-ray imaging apparatus is higher and higher, for example, having more functions and higher imaging quality; however, the current wireless connection manner can hardly satisfy higher demands on functions and quality, and is inconvenient for charging a detector. Comparing a wired connection method with a wireless method, the wired connection method may transmit data more reliably, has a better system stability, and may avoid removing the detector when it needs to be charged.

However, in order to facilitate the replacement with detectors of different sizes, a tray for supporting the detector is provided in a push-and-pull type, and a problem that needs to be solved is how to smoothly push and pull the tray and replace the detector while ensuring the reliability of the cable connection, and prevent movement of the tray and the cable from affecting each other.

SUMMARY

At least one object of the embodiments described herein is to provide a new X-ray imaging apparatus and a detector support device thereof, which can fulfil more imaging functions and facilitate data transmission and charging.

A non-limiting exemplary embodiment of the present disclosure provides a detector support device, the detector support device comprising a bracket, a slide tray, a detector tray for supporting a detector, a connector and a cable. The slide tray is installed on the bracket and is capable of sliding relative to the bracket. The detector tray is provided above the slide tray. The connector comprises a detector interface and a cable interface which are connected to each other, wherein the detector interface is installed on the detector tray so as to be connected to the detector, and an accommodation cavity, in which the cable interface is located, is opened from an upper surface of the slide tray. A first fixing portion fixed to a bottom wall of the accommodation cavity and a first bending portion extending from the first fixing portion to a first end of the cable are provided between the first end and a second end of the cable, the first end of the cable extends out of the slide tray so as to be connected to an external connector, and the second end of the cable is connected to the cable interface.

A further non-limiting embodiment provides an X-ray imaging apparatus comprising a detection bed and the above-mentioned detector support device, wherein the bracket of the detector support device is installed on the detection bed; the slide tray is capable of sliding into or out of the detection bed from a first side of the detection bed; the first end of the cable extends out of the slide tray so as to be connected to an external connector located on a second side of the detection bed; and the second side and the first end of the detection bed are opposite each other.

A further non-limiting embodiment provides an X-ray imaging apparatus comprising a chest-radiography stand and the above-mentioned detector support device, wherein the bracket of the detector support device is installed on the chest-radiography stand; the slide tray is capable of sliding into or out of the chest-radiography stand from a first side of the chest-radiography stand; the first end of the cable extends out of the slide tray so as to be connected to an external connector located on a second side of the chest-radiography stand; and the second side and the first side of the chest-radiography stand are opposite each other.

Other features and aspects will become apparent from the following detailed description, accompanying drawings and the claims.

BRIEF DESCRIPTION OF THE DRAWINGS

The present disclosure will be better understood by means of exemplary non-limiting embodiments described in conjunction with the accompanying drawings. In the drawings.

DETAILED DESCRIPTION

The specific embodiments of the present disclosure will be described below, and it should be noted that, in the specific description of these embodiments, for a concise description, the specification could not describe all the features of the practical implementations in detail. It should be understood that, in the practical implementation of any embodiment, just as in the course of any one engineering project or design project, in order to achieve the developers' specific goals and in order to meet system-related or business-related restrictions, a variety of specific decisions will be made accordingly, which will change from one embodiment to another embodiment. Furthermore, it should be understood that, although the efforts made in this development process may be complicated and lengthy, but for those skilled in the art related to the content disclosed in the present disclosure, some changes in the design, manufacture or production on the basis of the technical content disclosed in this disclosure are merely conventional technical means, and it should not be construed as the content of the present disclosure being insufficient.

Unless otherwise defined, technical or scientific terms used in the claims and description should be interpreted in the ordinary sense as understood by those of ordinary skill in the art to which this disclosure pertains. The terms "first", "second" and the like used in the specification and the claims in the present disclosure are merely used to distinguish different components, rather than denoting any order, quantity, or importance. The term "a" or "an" or the like denotes the presence of at least one, rather than representing a quantitative restriction. The term "comprising" or "including" or the like means that the element or object before the term "comprising" or "including" encompasses the element or object or equivalent element listed after the term "comprising" or "including", without excluding other elements or objects. The terms "connect" or "connected" and the like are neither limited to physical or mechanical connections, nor limited to direct or indirect connections.

Figure 1:
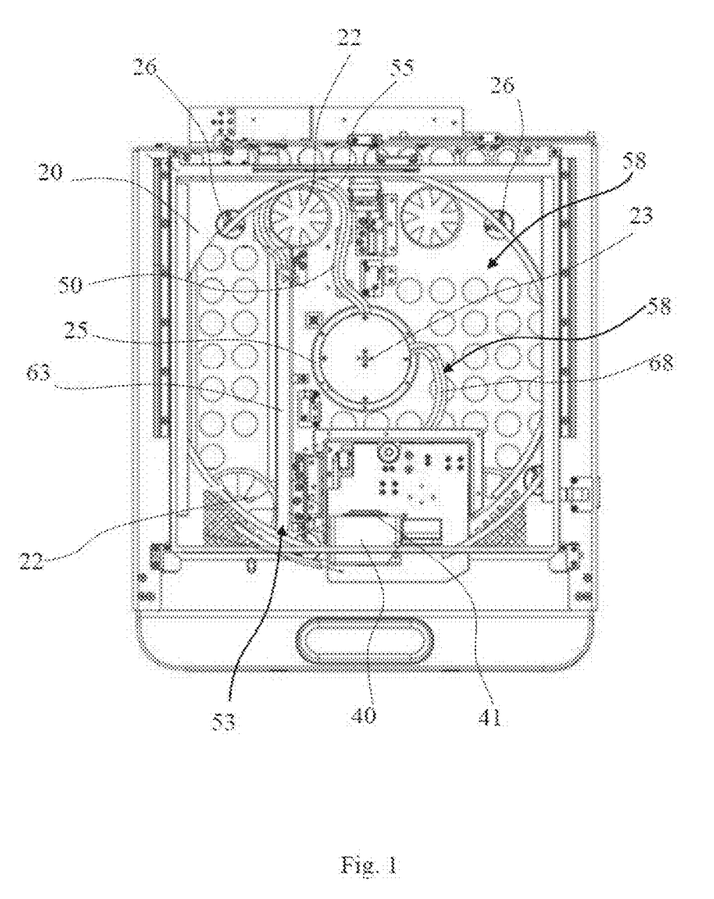
FIG. 1 is a structural schematic diagram of a detector support device according to an embodiment of the present disclosure.
Figure 2:
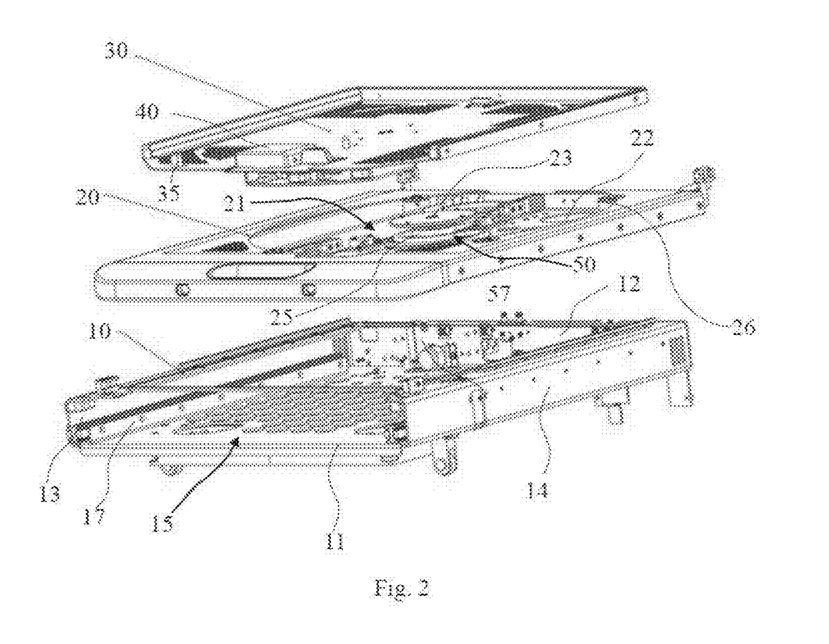
FIG. 2 is an exploded view of the detector support device in FIG. 1.

FIG. 1 is a structural schematic diagram of a detector support device provided in a non-limiting exemplary embodiment of the present disclosure, and FIG. 2 is an exploded view of the detector support device in FIG. 1; and as shown in FIGS. 1 and 2, the detector support device comprises a bracket 10, a slide tray 20, a detector tray 30, a connector 40 and a cable 50.

The bracket 10 may be provided below a bed surface of a detection bed, and the slide tray 20 is installed on the bracket 10 and is capable of sliding relative to the bracket 10. Specifically, the bracket 10 may comprise a bottom plate 11, a rear baffle 12 connected to the bottom plate 11 and two side plates 13 and 14, wherein the bottom plate, the rear baffle 12 and the two side plates 13 and 14 form a receiving space 16 with an opening 15, and the two side plates 13 and 14 are provided opposite each other and are respectively provided with a movement guiding component 17 thereon. Two sides of the slide tray 20 cooperate with movement components (not shown in the figures) of the movement guiding components, such that the slide tray 20 is capable of sliding from the opening 15 in a direction approaching or away from the rear baffle 12, and then sliding to a position below the detection bed or being exposed out of the detection bed. The above-mentioned movement guiding components 17 may include, for example, a slide rail; and the movement component may include, for example, a slide block.

An upper surface of the slide tray 20 is provided with an accommodation space 21. Specifically, the accommodation space 21 may be provided in various shapes according to requirements, for example, the accommodation space 21 may have side walls, and a bottom wall and an upper wall connected to two ends of the side walls, wherein the upper wall has an opening, so that it is convenient to arrange electronic elements or mechanical components in the accommodation space.

The detector tray 30 is provided above the slide tray, and is used for supporting a detector. The detector tray 30 may prevent the accommodation space 21 below from being exposed to the outside, thereby making the appearance of the detector support device concise, while serving a function of protecting components in the accommodation space 21.

Figure 3:
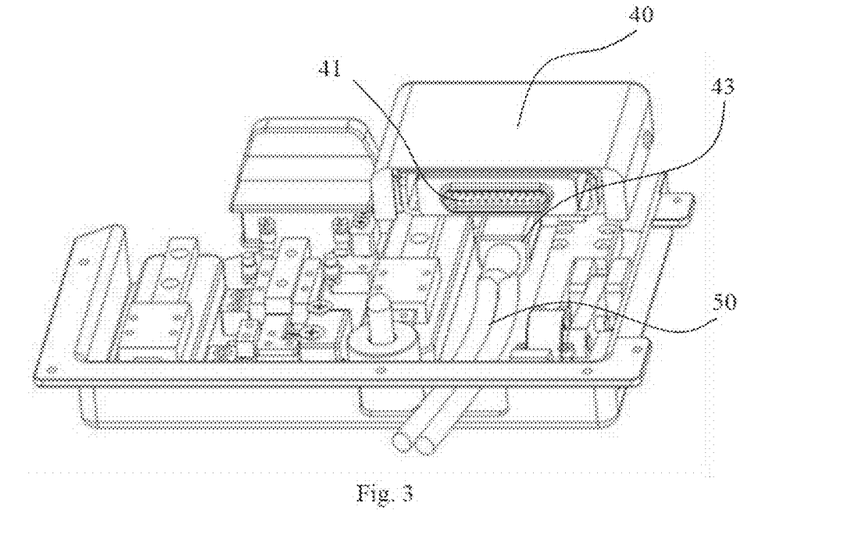
FIG. 3 is a structural schematic diagram of a connector in FIG. 1.
Figure 4:
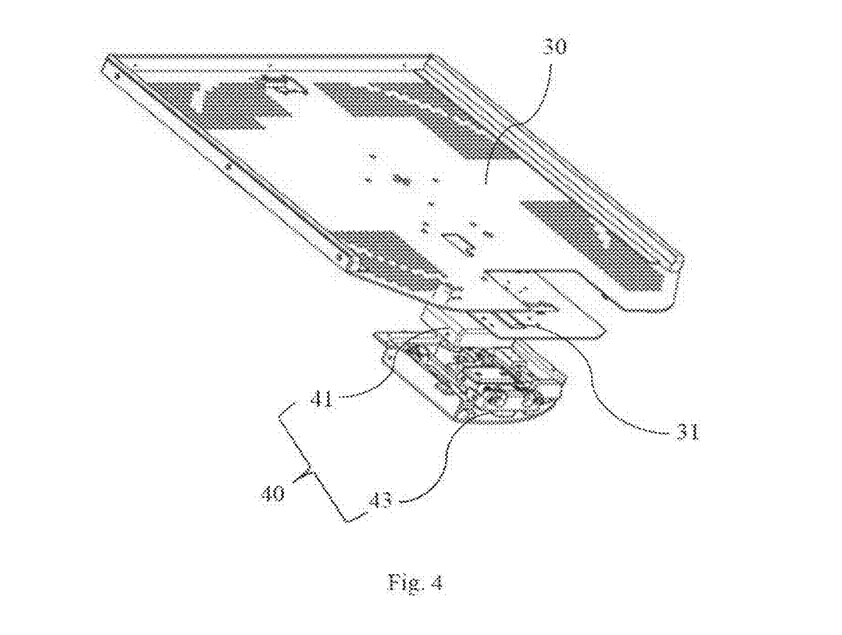
FIG. 4 is a structural schematic diagram of the connector and a detector tray in FIG. 1.

FIG. 3 is a structural schematic diagram of the connector in FIG. 1, and FIG. 4 is an installation structural schematic diagram of the connector and the detector tray in FIG. 1; and as shown in FIGS. 1-4, the connector 40 comprises a detector interface 41 and a cable interface 43 which are connected to each other, wherein the cable interface 43 is located in the accommodation cavity 21, and the detector interface 41 is installed on the detector tray 30 so as to be connected to the detector on the detector tray 30. For example, the detector interface 41 may be installed on the detector tray 30 so as to enable the detector interface 41 to be directly connected to the detector when the detector is fixed to the detector tray. It should be appreciated by those skilled in the art that the interconnection between the above-mentioned detector interface 43 and the cable interface 41 may include mechanical connection and electrical connection.

The cable 50 comprises a first end and a second end, wherein a first fixing portion 55 fixed to a bottom wall of the accommodation cavity 21 and a first bending portion 53 extending from the first fixing portion 55 to the first end are provided between the first end and the second end of the cable 50. The first end of the cable 50 may extend out of the slide tray 20 so as to be connected to an external connector, wherein the above-mentioned external connector may further be used for transmitting electric signals to a control unit of an X-ray imaging apparatus, such as a computer controller and a single-chip microcomputer. The second end of the cable 50 is used for being connected to the cable interface 43 of the connector 40. In this way, image signals emitted from the detector may be transmitted to the control unit of the X-ray imaging apparatus via the detector interface 41, the cable interface 43, the cable 50 and the external connector in sequence; and the control unit may analyse and process the image signals so as to form an image.

By forming the above-mentioned first fixing portion 55 and first bending portion 53 between the two ends of the cable 50, one end (namely, the first end 51 of the cable) of the first bending portion 53 is connected to the external connector; and in the process of the slide tray 20 moving relative to the bracket 10, the other end of the first bending portion 53 moves in cooperation with the slide tray 20 under the driving of the first fixing portion 55, so as to avoid from jeopardizing the reliability of signal connection due to considerable stretching and bending of the cable caused by tangling of the cable when freely pushing and pulling the slide tray.

Optionally, the detector tray 30 may be provided with a slot 31, and the cable interface 43 of the connector 40 may extend through the slot 31 so as to be located in the accommodation cavity 21. Specifically, the connector may be a U-shaped structure, and the detector interface 41 and the cable interface 43 may be respectively provided on two ends of the U-shaped structure. During installation, the cable interface 43 at one end of the U-shaped structure extends through the slot 31 so as to be located in the accommodation cavity 21 below the slot 31; the detector interface 41 at the other end of the U-shaped structure may be provided on an upper surface of the detector tray 30 and is located above the slot 31; an installation plate may be fixed to the bottom of the detector interface 41, wherein the installation plate may be installed on the upper surface of the detector tray 30 and span two sides of the slot 31, so that the slot 31 is shielded, avoiding exposing the accommodation cavity 21 to the outside. The installation plate may be configured in a slidable type so as to be applicable to detectors of different sizes on the detector tray 30.

By the above-mentioned methods, when the detector is fixed to the detector tray 30, it is convenient for the detector to be connected to the detector interface 41, which facilitates the replacement of the detector. By connecting the cable interface 43 and the detector interface 41 as a whole, connecting the cable interface 43 to the cable 50, and then providing the both in the accommodation cavity below the detector tray 30, component damage caused by an operator touching the cable 50 and the cable interface 43 for a long term is prevented, the reliability of the signal connection is ensured, and the appearance is simple.

Optionally, in a non-limiting exemplary embodiment of the present disclosure, the bottom wall of the accommodation cavity 21 may further be provided with a plurality of heat dissipation slots 22 for installing fans, wherein the above-mentioned first fixing portion 55 and the first bending portion 53 are respectively wound around two heat dissipation slots 22 provided opposite each other of the heat dissipation slots, for example, one of the heat dissipation slots 22 may be provided at a position near the rear baffle 12 of the bracket 10, the other heat dissipation slot 22 may be provided at a position away from the rear baffle 12; the first fixing portion 55 is wound outside the heat dissipation slot 22 near the rear baffle; and the first bending portion 53 is wound outside the other heat dissipation slot 22 away from the rear baffle 12. Specifically, the first fixing portion 55 may be a structure shaped like "C"; and a movement direction of the first bending portion 53 may be approximately the same as a sliding direction of the slide tray 20, for example, the first bending portion extending from the first fixing portion 55 is wound outside the heat dissipation slots 22 after extending towards the opening 15 of the bracket 10, and then extends out of the rear baffle 12 in an opposite direction so as to form a structure shaped like "U".

In order to fulfil more imaging functions, the above-mentioned detector tray 30 may be configured as a rotary tray, namely, driving, by rotating the detector tray 30, the detector thereon to rotate by a certain angle relative to the slide tray 20.

In order to enable the detector to rotate along with the detector tray 30, the detector interface 41 connected to the detector may be configured to be capable of rotating along with the detector tray 30. In the embodiment of the present disclosure, the above-mentioned connector 40 may be configured to be capable of rotating along with the detector tray 30.

Since the second end of the cable 50 is connected to the cable interface 43 of the connector 40, in order to avoid tangling, stretching, bending, etc. of the cable caused when the connector 40 rotates along with the rotation of the detector tray 30, a second fixing portion 57 extending out of the first fixing portion 55 and a second bending portion 58 extending from the second fixing portion 57 to the second end of the cable may be further provided between the first fixing portion 55 and the second end of the cable 50, wherein the second fixing portion 57 may be fixed to the bottom wall of the accommodation cavity 21.

By the above-mentioned second fixing portion 57 of the cable 50, one end (namely, the end connected to the second fixing portion 57) of the second bending portion 58 is fixed to the slide tray 20, the other end (namely, the end connected to the second end of the cable 50) may rotate in cooperation with the rotation of the detector tray 30, so as to avoid from jeopardizing the reliability of signal connection due to considerable stretching and bending of the cable caused by tangling of the cable when freely pushing and pulling the slide tray 30.

Optionally, the bottom wall of the above-mentioned accommodation cavity 21 may be provided with a support shaft 23, and the detector tray 30 may be pivotally connected to the support shaft 23 and may be configured to be capable of rotating around the support shaft 23. By the above-mentioned methods, the detector tray 30 may drive the detector and the connector 40 to rotate relative to the slide tray 20. Specifically, a protrusive handle 35 may be provided at a position, near an operator, of the upper surface of the detector tray 30, such that it is convenient for the operator to rotate the detector tray 30 via the protrusive handle 35.

Figure 5:
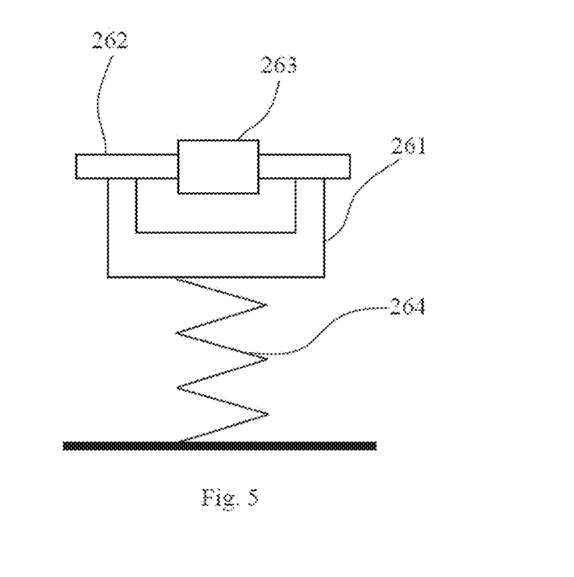
FIG. 5 is a structural schematic diagram of a floating support member in FIG. 2.

In order to enable the detector tray 30 to keep balance during rotation, in at least on embodiment the plurality of floating support members 26 may further be provided in the accommodation cavity 21. FIG. 5 is a structural schematic diagram of the floating support members 26 in FIG. 1; and as shown in FIG. 5, one end of each of the floating support members 26 is provided with a rolling member for being in contact with a bottom face of the detector tray 30, and the other end thereof is capable of elastically deforming under the pressure of the detector tray 30. For example, the floating support member 26 may comprise a support member 261, a support shaft 262, a bearing 263 and a spring 264, wherein two ends of the support shaft 262 are connected to the support member 261; the bearing 263, as the rolling member, is fitted around outside the support shaft 262 and is capable of rotating around the support shaft 262; one end of the spring 264 is fixed to the bottom of the support member, and the other end thereof is fixed to the bottom wall of the accommodation cavity 21; the bearing 263 is in contact with the bottom face of the detector tray 30 so as to support the detector tray 20 and avoid the tilt of the detector tray; the pressure generated by the rotation of the detector tray 30 on the bearing 263 and the elasticity of the spring 264 enable the detector tray 30 to be capable of floating up and down within a certain range; and the detector tray 30 rolls or rotates during rotation by cooperating with the bearing 263, so that the detector tray 30 is subject to smaller resistance in the process of rotation.

A position of the above-mentioned support shaft 23 on the slide tray 20 may be opposite a geometric centre of the detector, namely, the above-mentioned support shaft 23 may be roughly provided at a central position of the accommodation cavity 21 so as to facilitate rotation and satisfy imaging requirements.

Optionally, the above-mentioned second fixing portion 58 may be wound around the support shaft 23 with the support shaft 23 as a centre, thus avoiding increasing the length of the cable, and further avoiding the tangling or stretching of the cable caused during rotation.

Specifically, a bearing 25 may be provided on the bottom wall of the accommodation cavity 21, wherein the bearing 25 is fitted around the support shaft 23, and the second fixing portion 58 may be provided on the bearing 25 so as to optimize the spatial layout of the accommodation cavity 21.

In order to further optimize the spatial layout, improve the reliability of the signal connection and avoid the tangling, stretching, bending etc. of the cable, in an overall view, the above-mentioned plurality of heat dissipation slots 22 may be provided around the accommodation cavity 21, namely, being distributed around the support shaft 23 and the bearing 25 thereof. The above-mentioned first fixing portion 55 and first bending portion 53 may be roughly located on the left side of the support shaft 23 and the bearing 25 thereof (for example, the first fixing portion is close to the rear baffle 12 and the side plate 13 of the bracket 10, and the first bending portion 53 is close to the side plate 13 and the opening 15 of the bracket 10); and the second bending portion may be roughly located on a right side of the support shaft 23 and the bearing 25 thereof (for example, the second bending portion 58 is close to the side plate 14 of the bracket 10).

At least one of the above-mentioned first fixing portion 55 and the second fixing portion 57 is designed as an arc-shaped structure with an opening, wherein the arc-shaped structure may comprise, for example, a C-shape. At least one of the above-mentioned first bending portion 53 and the second bending portion 58 may also be designed as an arc-shaped structure with an opening, wherein the arc-shaped structure may include, for example, a U-shape. The above-mentioned "an arc-shaped structure with an opening" may refer to that the arc-shaped structure is not closed. Designing the first fixing portion 55, the second fixing portion 57, the first bending portion 53 and the second bending portion 58 as an arc-shaped structure resembling a C-shape and a U-shape can reduce the difficulty in fixing the cable, protect the cable from excessive bending, avoid crossing of the cable, and can further enable the first bending portion 53 to move more smoothly in cooperation with the movement of the slide tray 20, and enable the second bending portion 55 to rotate more smoothly in cooperation with the rotation of the detector tray 40.

Further, the first fixing portion 55 and the first bending portion 53 form an S-shaped structure, the second fixing portion 57 and the first bending portion 58 form an S-shaped structure, and the first fixing portion 55 and the second fixing portion 57 form an S-shaped structure. In this way, the spatial layout can be optimized, and moreover, it can be ensured that the movement of the cable is free from being affected by itself and other components.

The "C-shape", "U-shape" and "S-shape" described in the present embodiment refer to shapes resembling a "C-shape", a "U-shape" and a "S-shape", and therefore, are not restricted to a standard "C-shape", "U-shape" and "S-shape", and may be modified structures of these standard shapes, as long as the modified structures roughly comply with the flow direction of the line.

Optionally, in the embodiments of the present disclosure, a tank chain may further be provided, the tank chain being used for accommodating at least one of the first bending portion 53 and the second bending portion 58. For example, as shown in FIG. 1, the first bending portion 53 may be provided in a first tank chain 63, and the second bending portion 58 may be provided in a second tank chain 68, wherein two ends of the first tank chain 63 and the second tank chain 68 may be fixed to the slide tray 20. By arranging the tank chain, the first bending portion 53 may be guided to move more accurately along a set direction (such as the sliding direction of the slide tray 20) in the process of the slide tray 20 sliding; the second bending portion 58 may also be guided to move more accurately along the set direction (such as the rotation direction of the detector tray 30) when rotating the detector tray 30; and therefore, the cable 50 does not break and tangle easily, thereby improving the stability of the system.

The non-limiting exemplary embodiments of the present disclosure further provide an X-ray imaging apparatus which may comprise a detection bed (not shown in the figures) and the detector support device in the above-mentioned embodiment. The bracket 10 of the detector support device may be installed on the detection bed, and specifically, may be installed at the back of the detection bed and is opposite a bed surface of the detection bed, or a slot is provided below the bed surface of the detection bed along a side face of the detection bed, and the bracket 10 is provided in the slot so as to enable the detector support device to be provided below the bed surface of the detection bed. Since the slide tray 20 is capable of sliding into or out of the bracket, the slide tray 20 is also capable of sliding into or out of the detection bed from a first side of the detection bed, and the first end 51 of the cable 50 extends out of the slide tray 20 so as to be connected to an external connector located on a second side of the detection bed. The above-mentioned first side and second side of the detection bed are opposite each other, wherein the first side of the detection bed may be a side close to an operator, and the second side of the detection bed may be a side away from the operator.

It should be appreciated by those skilled in the art that the X-ray imaging apparatus may further comprise an X-ray bulb tube, wherein the X-ray bulb tube may be arranged on an upright column or a suspension system so as to be located above the bed surface of the detection bed, and is opposite a detector on the detector support device, so that X-rays emitted by the X-ray bulb tube, after penetrating a human body, may be received by the detector.

While the technical solution of installing the detector support device of the present disclosure on the detection bed is described above, it should be appreciated by those skilled in the art that the detector support device may also be installed on a chest-radiography stand; therefore, the embodiment of the disclosure may further provide an X-ray imaging apparatus which comprises a chest-radiography stand and the above-mentioned detector support device, wherein the bracket 10 of the detector support device is installed on the chest-radiography stand; the slide tray 20 is capable of sliding into or out of the chest-radiography stand from a first side of the chest-radiography stand; and the first end of the cable 50 extends out of the slide tray so as to be connected to an external connector located on a second side of the chest-radiography stand, wherein the second side and the first side of the chest-radiography stand is opposite each other.

The detector support device and the X-ray imaging apparatus provided in the embodiments of the present disclosure, by adopting cable connection between the external connector and the detector, the stability of signal transmission is improved, off-line charging is avoided, and more imaging functions can be realized. The cable is provided in the accommodation cavity of the slide tray on which the detector tray is provided, thereby avoiding various inconvenience and the instability of the signal connection caused by the cable being exposed to the outside. A detector connector and a cable connector are connected to each other, and are respectively located on an upper side and a lower side of the detector tray, so that the whole signal connection is completed after enabling the detector to be connected to the detector interface without other operations, thus improving the stability of signal transmission. The cable is configured to have a fixing portion and a bending portion, thus prevent the cable from bending, tangling, crossing, stretching, etc. by means of cooperative movement during the sliding of the slide tray and the rotation of the detector tray, which further ensures the stability of the signal transmission. In addition, the detector support device and the X-ray imaging apparatus having the detector support device in the embodiments of the present disclosure have, as a whole, are simple in appearance and compact in structural design, thereby saving on space.

Some exemplary embodiments have been described above. However, it should be understood that various changes may be made. For example, if the described techniques are performed in a different order and/or if the components in the described systems, architectures, apparatuses or circuits are combined in different ways and/or replaced or supplemented by additional components or their equivalents, an appropriate result can be achieved. Accordingly, other embodiments also fall within the scope of protection of the claims.

What is claimed is:

1. A detector support device, comprising:
   a slide tray installed on a bracket and slidable relative to the bracket, the slide tray comprising an accommodation cavity;
   a detector tray configured to support a detector, wherein the detector tray comprises a slot;
   a connector comprising a detector interface and a cable interface which are connected to each other, wherein the cable interface is configured to be located in the accommodation cavity, and the detector interface is installed on the detector tray and configured to connect to the detector, wherein the detector interface and the cable interface are vertically aligned relative to each other along a plane extending from the detector tray to the slide tray, and the cable interface passes through and below the slot of the detector array into the accommodation cavity; and
   a cable, comprising a first end and a second end, wherein a first fixing portion fixed to the accommodation cavity and a first bending portion extending from the first fixing portion to the first end are provided between the first end and the second end of the cable, the first end of the cable is configured to extend out of the slide tray to connect to an external connector, and the second end of the cable is configured to connect to the cable interface.

2. The detector support device according to claim 1, wherein a second fixing portion extending from the first fixing portion and a second bending portion extending from the second fixing portion to the second end are provided between the first fixing portion and the second end, and the second fixing portion is fixed to the bottom wall of the accommodation cavity.

3. The detector support device according to claim 2, wherein the connector is configured to rotate along with the detector tray.

4. The detector support device according to claim 3, wherein a bottom wall of the accommodation cavity is provided with a support shaft, and the detector tray is pivotally connected to the support shaft and is configured to rotate around the support shaft.

5. The detector support device according to claim 4, wherein the second fixing portion is wound outside the support shaft with the support shaft as a center point.

6. The detector support device according to claim 4, wherein the bottom wall of the accommodation cavity is further provided with a bearing fitted around the support shaft, and the second fixing portion is provided on the bearing.

7. The detector support device according to claim 4, wherein a plurality of floating support members are provided in the accommodation cavity, wherein one end of each of the floating support members is provided with a rolling member which is in contact with a bottom face of the detector tray, and the other end thereof is deformable elastically under a pressure applied by the detector tray.

8. The detector support device according to claim 2, wherein at least one of the first fixing portion and the second fixing portion is an arc-shaped structure with an opening, and at least one of the first bending portion and the second bending portion is an arc-shaped structure with an opening.

9. The detector support device according to claim 2, wherein the first fixing portion and the first bending portion form an S-shaped structure, the second fixing portion and the first bending portion form an S-shaped structure, and the first fixing portion and the second fixing portion form an S-shaped structure.

10. The detector support device according to claim 2, further comprising a tank chain for accommodating at least one of the first bending portion and the second bending portion.

11. The detector support device according to claim 1, wherein the connector is a U-shaped structure defining two ends, and the detector interface and the cable interface are respectively provided at the two ends of the U-shaped structure.

12. The detector support device according to claim 1, wherein a plurality of heat dissipation slots are provided along the bottom wall of the accommodation cavity, and the first fixing portion and the first bending portion are respectively wound outside at least two of the plurality heat dissipation slots.

13. An X-ray imaging apparatus, comprising a detection bed and a detector support device according to claim 1, wherein the bracket of the detector support device is installed on the detection bed, the slide tray is configured to slide into or out of the detection bed from a first side of the detection bed, and the first end of the cable extends out of the slide tray to connect to an external connector located on a second side of the detection bed.

14. An X-ray imaging apparatus, comprising a chest-radiography stand and a detector support device according to claim 1, wherein the bracket of the detector support device is installed on the chest-radiography stand, the slide tray is configured to slide into or out of the chest-radiography stand from a first side of the chest-radiography stand, and the first end of the cable extends out of the slide tray to connect to an external connector located on a second side of the chest-radiography stand.

15. A detector support device, comprising:
   a slide tray installed on a bracket and slidable relative to the bracket, the slide tray comprising an accommodation cavity;
   a detector tray configured to support a detector;
   a connector comprising a detector interface and a cable interface which are connected to each other, wherein the cable interface is configured to be located in the accommodation cavity, and the detector interface is installed on the detector tray and configured to connect to the detector; and
   a cable, comprising a first end and a second end, wherein a first fixing portion fixed to the accommodation cavity and a first bending portion extending from the first fixing portion to the first end are provided between the first end and the second end of the cable, the first end of the cable is configured to extend out of the slide tray to connect to an external connector, and the second end of the cable is configured to connect to the cable interface;

wherein a second fixing portion extending from the first fixing portion and a second bending portion extending from the second fixing portion to the second end are provided between the first fixing portion and the second end, and the second fixing portion is fixed to the bottom wall of the accommodation cavity;

wherein the connector is configured to rotate along with the detector tray;

wherein a bottom wall of the accommodation cavity is provided with a support shaft, and the detector tray is pivotally connected to the support shaft and is configured to rotate around the support shaft;

wherein the second fixing portion is wound outside the support shaft with the support shaft as a center point; and wherein the bottom wall of the accommodation cavity is further provided with a bearing fitted around the support shaft, and the second fixing portion is provided on the bearing.

16. A detector support device, comprising:
a slide tray installed on a bracket and slidable relative to the bracket, the slide tray comprising an accommodation cavity;
a detector tray configured to support a detector;
a connector comprising a detector interface and a cable interface which are connected to each other, wherein the cable interface is configured to be located in the accommodation cavity, and the detector interface is installed on the detector tray and configured to connect to the detector; and
a cable, comprising a first end and a second end, wherein a first fixing portion fixed to the accommodation cavity and a first bending portion extending from the first fixing portion to the first end are provided between the first end and the second end of the cable, the first end of the cable is configured to extend out of the slide tray to connect to an external connector, and the second end of the cable is configured to connect to the cable interface;
wherein a second fixing portion extending from the first fixing portion and a second bending portion extending from the second fixing portion to the second end are provided between the first fixing portion and the second end, and the second fixing portion is fixed to the bottom wall of the accommodation cavity;
wherein the connector is configured to rotate along with the detector tray;
wherein a bottom wall of the accommodation cavity is provided with a support shaft, and the detector tray is pivotally connected to the support shaft and is configured to rotate around the support shaft;
wherein the second fixing portion is wound outside the support shaft with the support shaft as a center point; and
wherein a plurality of floating support members are provided in the accommodation cavity, wherein one end of each of the floating support members is provided with a rolling member which is in contact with a bottom face of the detector tray, and the other end thereof is deformable elastically under a pressure applied by the detector tray.

17. A detector support device, comprising:
a slide tray installed on a bracket and slidable relative to the bracket, the slide tray comprising an accommodation cavity;
a detector tray configured to support a detector;
a connector comprising a detector interface and a cable interface which are connected to each other, wherein the cable interface is configured to be located in the accommodation cavity, and the detector interface is installed on the detector tray and configured to connect to the detector; and
a cable, comprising a first end and a second end, wherein a first fixing portion fixed to the accommodation cavity and a first bending portion extending from the first fixing portion to the first end are provided between the first end and the second end of the cable, the first end of the cable is configured to extend out of the slide tray to connect to an external connector, and the second end of the cable is configured to connect to the cable interface, and wherein a second fixing portion extending from the first fixing portion and a second bending portion extending from the second fixing portion to the second end are provided between the first fixing portion and the second end, and the second fixing portion is fixed to the bottom wall of the accommodation cavity; and
a tank chain for accommodating at least one of the first bending portion and the second bending portion.

18. A detector support device, comprising:
a slide tray installed on a bracket and slidable relative to the bracket, the slide tray comprising an accommodation cavity;
a detector tray configured to support a detector;
a connector comprising a detector interface and a cable interface which are connected to each other, wherein the cable interface is configured to be located in the accommodation cavity, and the detector interface is installed on the detector tray and configured to connect to the detector; and
a cable, comprising a first end and a second end, wherein a first fixing portion fixed to the accommodation cavity and a first bending portion extending from the first fixing portion to the first end are provided between the first end and the second end of the cable, the first end of the cable is configured to extend out of the slide tray to connect to an external connector, and the second end of the cable is configured to connect to the cable interface;
wherein a plurality of heat dissipation slots are provided along the bottom wall of the accommodation cavity, and the first fixing portion and the first bending portion are respectively wound outside at least two of the plurality heat dissipation slots.

* * * * *